(12) United States Patent
Baker et al.

(10) Patent No.: US 8,894,670 B2
(45) Date of Patent: Nov. 25, 2014

(54) MUCOSAL CAPTURE FIXATION OF MEDICAL DEVICE

(75) Inventors: Randal S. Baker, Ada, MI (US); James A. Foote, Ada, MI (US); Paul R. Kemmeter, Ada, MI (US); Frederick J. Walburn, Grand Rapids, MI (US)

(73) Assignee: BFKW, LLC, Grand Rapids, MI (US)

( * ) Notice: Subject to any disclaimer, the term of this patent is extended or adjusted under 35 U.S.C. 154(b) by 849 days.

(21) Appl. No.: 12/540,619

(22) Filed: Aug. 13, 2009

(65) Prior Publication Data

US 2010/0198237 A1 Aug. 5, 2010

Related U.S. Application Data

(63) Continuation-in-part of application No. PCT/US2008/053797, filed on Feb. 13, 2008.

(60) Provisional application No. 60/901,457, filed on Feb. 14, 2007, provisional application No. 60/921,930, filed on Apr. 5, 2007, provisional application No. 61/015,258, filed on Dec. 20, 2007.

(51) Int. Cl.
*A61B 17/00* (2006.01)
*A61F 2/04* (2013.01)

(52) U.S. Cl.
CPC .................................. *A61F 2/04* (2013.01)
USPC ........................................................ 606/153

(58) Field of Classification Search
USPC ............ 606/213, 153–156; 623/23.64–23.68, 623/23.7; 600/37; 128/898
See application file for complete search history.

(56) References Cited

U.S. PATENT DOCUMENTS

| 4,403,604 A | 9/1983 | Wilkinson et al. |
| 4,607,618 A | 8/1986 | Angelchik |
| 5,234,454 A | 8/1993 | Bangs |

(Continued)

FOREIGN PATENT DOCUMENTS

| RU | 2045233 C1 | 10/1995 |
| RU | 94026119 A1 | 8/1996 |

(Continued)

OTHER PUBLICATIONS

International Preliminary Report on Patentability from corresponding Patent Cooperation Treaty (PCT) Patent Application No. PCT/US08/53797, mailed Aug. 27, 2009.

(Continued)

*Primary Examiner* — Darwin Erezo
*Assistant Examiner* — Shaun L David
(74) *Attorney, Agent, or Firm* — Gardner, Linn, Burkhart & Flory, LLP

(57) ABSTRACT

An implantable medical device and method of implanting a medical device in a hollow organ or cavity lined with the mucosa includes providing a medical device having a wall configured to the size and shape of a portion of a cavity or hollow organ lined with the mucosa. At least one opening is provided in the wall that is large enough to receive a section of the mucosa extending in the opening. The wall is positioned against the portion of the cavity or hollow organ thereby receiving the section of the mucosa within the opening. A retainer may be provided to retain the section of the mucosa within the opening while maintaining perfusion of the section of the mucosa.

19 Claims, 3 Drawing Sheets

(56) References Cited

U.S. PATENT DOCUMENTS

| | | | |
|---|---|---|---|
| 5,306,300 A | 4/1994 | Berry | |
| 5,507,755 A | 4/1996 | Gresl et al. | |
| 5,662,713 A | 9/1997 | Andersen et al. | |
| 5,741,279 A | 4/1998 | Gordon et al. | |
| 5,820,584 A | 10/1998 | Crabb | |
| 6,432,040 B1 | 8/2002 | Meah | |
| 6,544,291 B2 | 4/2003 | Taylor | |
| 6,558,400 B2 | 5/2003 | Deem et al. | |
| 6,572,627 B2 | 6/2003 | Gabbay | |
| 6,656,194 B1 | 12/2003 | Gannoe et al. | |
| 6,675,809 B2 | 1/2004 | Stack et al. | |
| 6,736,828 B1* | 5/2004 | Adams et al. | 606/213 |
| 6,740,121 B2 | 5/2004 | Geitz | |
| 6,746,460 B2 | 6/2004 | Gannoe et al. | |
| 6,755,869 B2 | 6/2004 | Geitz | |
| 6,773,440 B2 | 8/2004 | Gannoe et al. | |
| 6,802,868 B2 | 10/2004 | Silverman et al. | |
| 6,845,776 B2 | 1/2005 | Stack et al. | |
| 6,960,233 B1 | 11/2005 | Berg et al. | |
| 6,981,978 B2 | 1/2006 | Gannoe | |
| 6,994,095 B2 | 2/2006 | Burnett | |
| 6,994,715 B2 | 2/2006 | Gannoe et al. | |
| 7,025,791 B2 | 4/2006 | Levine et al. | |
| 7,033,373 B2 | 4/2006 | de la Torre et al. | |
| 7,033,384 B2 | 4/2006 | Gannoe et al. | |
| 7,037,344 B2 | 5/2006 | Kagan et al. | |
| 7,044,979 B2 | 5/2006 | Silverman et al. | |
| 7,066,945 B2 | 6/2006 | Hashiba et al. | |
| 7,083,629 B2 | 8/2006 | Weller et al. | |
| 7,083,630 B2 | 8/2006 | DeVries et al. | |
| 7,087,088 B2 | 8/2006 | Berg et al. | |
| 7,097,650 B2 | 8/2006 | Weller et al. | |
| 7,097,665 B2 | 8/2006 | Stack et al. | |
| 7,146,984 B2 | 12/2006 | Stack et al. | |
| 7,152,607 B2 | 12/2006 | Stack et al. | |
| 7,220,284 B2 | 5/2007 | Kagan et al. | |
| 7,431,725 B2 | 10/2008 | Stack et al. | |
| 7,445,010 B2 | 11/2008 | Kugler et al. | |
| 7,708,752 B2 | 5/2010 | Durgin | |
| 7,846,174 B2 | 12/2010 | Baker et al. | |
| 8,029,455 B2 | 10/2011 | Stack et al. | |
| 8,100,931 B2 | 1/2012 | Baker et al. | |
| 8,372,087 B2 | 2/2013 | Baker et al. | |
| 2001/0020189 A1 | 9/2001 | Taylor | |
| 2002/0032487 A1 | 3/2002 | Dua et al. | |
| 2002/0091395 A1 | 7/2002 | Gabbay | |
| 2003/0065359 A1* | 4/2003 | Weller et al. | 606/213 |
| 2003/0199989 A1* | 10/2003 | Stack et al. | 623/23.65 |
| 2004/0117031 A1 | 6/2004 | Stack et al. | |
| 2004/0138761 A1 | 7/2004 | Stack et al. | |
| 2004/0143342 A1 | 7/2004 | Stack et al. | |
| 2004/0172141 A1* | 9/2004 | Stack et al. | 623/23.65 |
| 2004/0220682 A1 | 11/2004 | Levine et al. | |
| 2005/0197715 A1 | 9/2005 | Kugler et al. | |
| 2005/0228504 A1 | 10/2005 | Demarais | |
| 2005/0245788 A1 | 11/2005 | Gerber | |
| 2005/0245957 A1 | 11/2005 | Starkebaum et al. | |
| 2005/0247320 A1* | 11/2005 | Stack et al. | 128/898 |
| 2005/0251176 A1 | 11/2005 | Swanstrom et al. | |
| 2005/0283235 A1 | 12/2005 | Kugler et al. | |
| 2006/0020277 A1 | 1/2006 | Gostout et al. | |
| 2006/0036293 A1 | 2/2006 | Whitehurst et al. | |
| 2006/0074473 A1 | 4/2006 | Gertner | |
| 2006/0089571 A1 | 4/2006 | Gertner | |
| 2006/0149307 A1 | 7/2006 | Durgin | |
| 2006/0155375 A1 | 7/2006 | Kagan et al. | |
| 2006/0190019 A1 | 8/2006 | Gannoe et al. | |
| 2006/0253131 A1 | 11/2006 | Wolniewicz, III | |
| 2006/0264699 A1 | 11/2006 | Gertner | |
| 2007/0010866 A1 | 1/2007 | Dann et al. | |
| 2007/0166396 A1 | 7/2007 | Badylak et al. | |
| 2007/0179590 A1 | 8/2007 | Lu et al. | |
| 2007/0208429 A1 | 9/2007 | Leahy | |
| 2007/0276432 A1 | 11/2007 | Stack et al. | |
| 2007/0293716 A1 | 12/2007 | Baker et al. | |
| 2008/0015523 A1 | 1/2008 | Baker | |
| 2008/0065136 A1 | 3/2008 | Young | |
| 2008/0215076 A1 | 9/2008 | Baker | |
| 2008/0312678 A1 | 12/2008 | Pasricha | |
| 2009/0177215 A1 | 7/2009 | Stack et al. | |
| 2010/0030017 A1 | 2/2010 | Baker et al. | |
| 2010/0063518 A1 | 3/2010 | Baker et al. | |
| 2010/0114124 A1* | 5/2010 | Kelleher et al. | 606/151 |
| 2010/0198237 A1 | 8/2010 | Baker et al. | |
| 2011/0092879 A1 | 4/2011 | Baker et al. | |
| 2012/0089168 A1 | 4/2012 | Baker et al. | |
| 2012/0289991 A1 | 11/2012 | Baker | |
| 2013/0123811 A1 | 5/2013 | Baker et al. | |

FOREIGN PATENT DOCUMENTS

| | | |
|---|---|---|
| WO | 0135834 A1 | 5/2001 |
| WO | 0185034 A1 | 11/2001 |
| WO | 02060328 A1 | 8/2002 |
| WO | 02094105 A1 | 11/2002 |
| WO | 2004064685 A1 | 8/2004 |
| WO | 2005037152 A1 | 4/2005 |
| WO | 2006044640 A1 | 4/2006 |

OTHER PUBLICATIONS

U.S. Appl. No. 13/331,425, filed Dec. 20, 2011, entitled Bariatric Device and Method, has at least one inventor in common with the present application and is assigned to an entity having shareholders in common with the present application.

"Obesity: Super-Sized Medical Device Market", Start-Up, Mar. 2003, Technology Strategies (Long Article), pp. 1-10.

Andrew S. Lowe, M.D. and Maria B. Sheridan, M.D., "Esphogeal Stenting", Seminars in Interventional Radiology, vol. 21, No. 3, 2004, pp. 157-166.

"Polyflex® Espohageal Stent", Silicone Covered Stent, Boston Scientific, pp. 1-2 and p. 1 of 2 (2004).

Andrew F.R. Dixon, John B. Dixon, and Paul E. O'Brien, "Laparoscopic Adjustable Gastric Banding Induces Prolonged Satiety: A Randomized Blind Crossover Study", The Journal of Clinical Endocrinology & Metabolism, pp. 813-819, 2005.

Roman, S. et al., "Intragastric balloon for 'non-morbid' obesity: a retrospective evaluation of tolerance and efficacy," Obes. Surg., 2004, 14(4), 539-44, abstract, [on-line], [found Apr. 17, 2009, from Pubmed database].

Busetto, L. et al., "Preoperative weight loss by intragastric balloon in super-obese patients treated with laparoscopic gastric banding: a case-control study," Obes Surg., 2004, 14(5), 671-6, abstract, [on-line], [found Apr. 17, 2009, from Pubmed database].

International Search Report and Written Opinion of the International Searching Authority from corresponding Patent Cooperation Treaty (PCT) Application No. PCT/US05/36991, mailed Mar. 31, 2006.

Summary of Official Action dated Oct. 29, 2009, from the Israel Patent Office in a patent application corresponding to the present application.

Lowe, Andrew S., M.D. and Sheridan, Maria B., M.D., "Esophageal Stenting," annotated by Israel Patent Office (2004).

Abstract and claims of U.S. Patent 6,960,233 annotated by the Israel Patent Office (Nov. 1, 2005).

International Search Report and Written Opinion of the International Searching Authority from corresponding Patent Cooperation Treaty (PCT) Application No. PCT/US08/53797, mailed Aug. 7, 2008.

Commonly assigned co-pending U.S. Appl. No. 13/965,617, filed Aug. 13, 2013, entitled Bariatric Device and Method.

Commonly assigned co-pending U.S. Appl. No. 13/876,564, filed Sep. 30, 2011, entitled Intraluminal Device and Method.

* cited by examiner

MUCOSAL CAPTURE FIXATION OF MEDICAL DEVICE

CROSS REFERENCE TO RELATED APPLICATIONS

This application is a continuation-in-part of International Patent Application No. PCT/US08/53797, filed on Feb. 13, 2008, which claims priority from U.S. provisional patent application Ser. No. 60/901,457 filed on Feb. 14, 2007; U.S. provisional patent application Ser. No. 60/921,930, filed on Apr. 5, 2007; and U.S. provisional patent application Ser. No. 61/015,258, filed on Dec. 20, 2007, the disclosures of which are hereby incorporated herein by reference in their entireties.

BACKGROUND OF THE INVENTION

The present invention is directed to an implantable medical device and a method of affixing an implantable medical device. The invention has application to gastrointestinal devices and to other devices that are implanted in a patient's hollow organ or cavity that is accessible through a natural orifice.

Medical devices often require fixation in patients, whether the device is intended to be in place temporarily, permanently, or semi-permanently. Fixation often needs to be strong, particularly where the device experiences a shear force, such as in the presence of peristalsis. However, fixation to the wall of certain hollow organs or cavities may be difficult due to, for example, localized tension applied to the wall. As a result, attachment could fail or lead to ulceration, or the like.

SUMMARY OF THE INVENTION

An implantable medical device and method of implanting a medical device in a hollow organ or cavity lined with the mucosa, according to an aspect of the invention, includes providing a medical device having a wall configured to the size and shape of a portion of a cavity or hollow organ lined with the mucosa. At least one opening is provided in the wall that is large enough to receive a section of the mucosa extending in the opening. The wall is positioned against the portion of the cavity or hollow organ thereby receiving the section of the mucosa within the opening.

The device may include a retainer that retains the section of the mucosa within the at least one opening while maintaining perfusion of the section of the mucosa. The retainer may include a penetrating component, a pressure component, or both. Such penetrating component is adapted to penetrate the section of the mucosa in the at least one opening. Such pressure component is adapted to put pressure on the section of the mucosa in the at least one opening. The wall of the device may have an outer surface and an inner surface, with the inner surface defining a lumen. The retainer may be accessible from within the lumen to detach the wall from the mucosa.

The at least one opening may be a plurality of openings and the penetrating component may include a plurality of penetrating components, one for retaining the section of the mucosa within each of the openings. Alternatively, the penetrating component may include an elongated member that penetrates the sections of the mucosa at the plurality of openings. The elongated member may be a suture, a needle, or the like.

The at least one opening may be defined between two moveable portions of the wall, wherein the pressure component is made up of moveable portions being adapted to move together. A penetrating component may be provided at one of the moveable portions and extending into the at least one opening. The penetrating component may be made up of a plurality of pointed members extending into the at least one opening from at least one of said moveable portions. The wall may be in a generally tubular shape and the opening may span the length of the wall in the direction of an axis of the tubular shape.

The at least one opening may include at least two of openings that are closely spaced and the retainer may retain the sections of the mucosa bridging the at least two openings. The retainer may include a clip, a fusion agent, such as a sclerosant, or the like.

The retainer may include a fibrotic tissue response inducing material at least partially surrounding the at least one opening.

The retainer may be made at least in part from a bioabsorbable material or from a non-absorbable material.

The wall may be a generally impervious surface having a surface area that is larger than an area of the at least one opening. The at least one opening may have a width or diameter that is at least on an order of magnitude of 1 millimeter.

The device may be an esophageal stent, a bariatric device, an anti-reflux device, a nasal gastric tube, an intestinal sleeve, or the like.

These and other objects, advantages and features of this invention will become apparent upon review of the following specification in conjunction with the drawings.

DESCRIPTION OF THE PREFERRED EMBODIMENT

Figure 1:
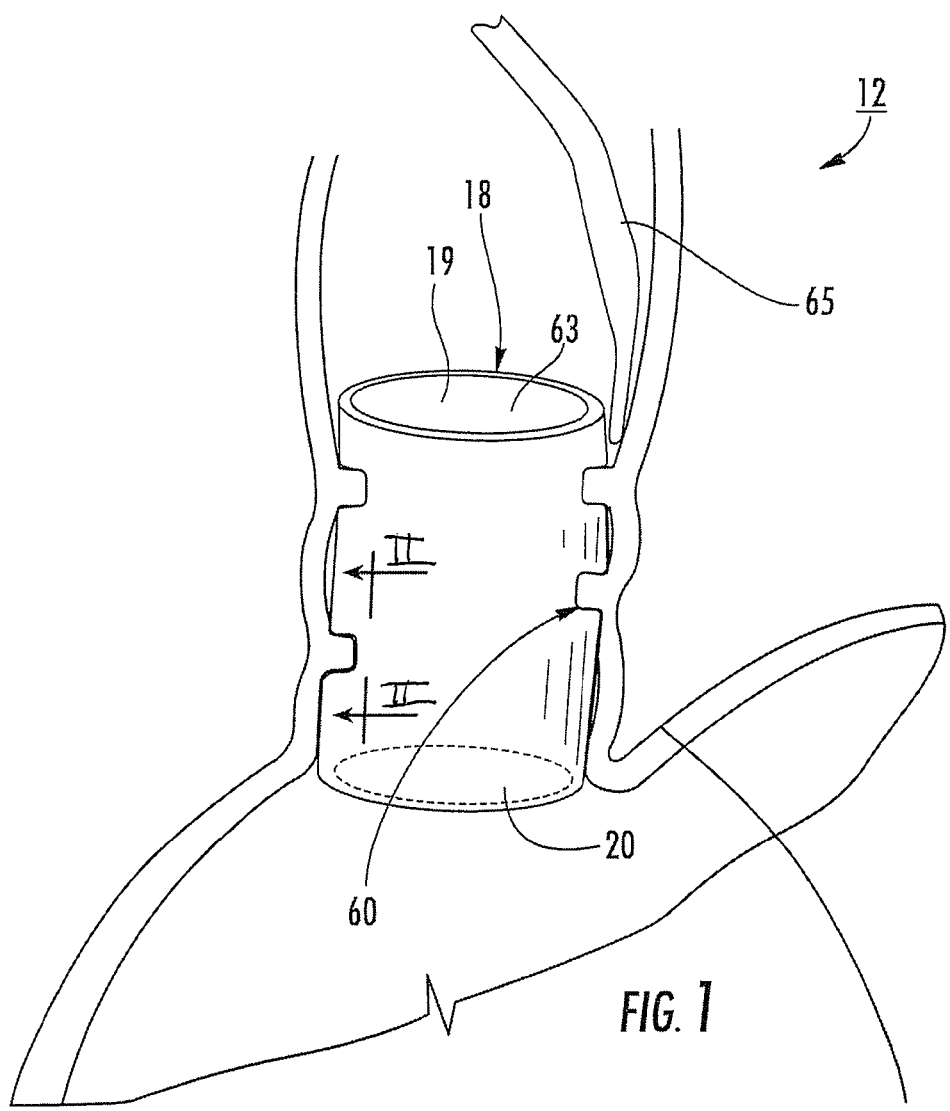
FIG. 1 is a perspective view of an embodiment of mucosal capture fixation of a medical device.
Figure 2:
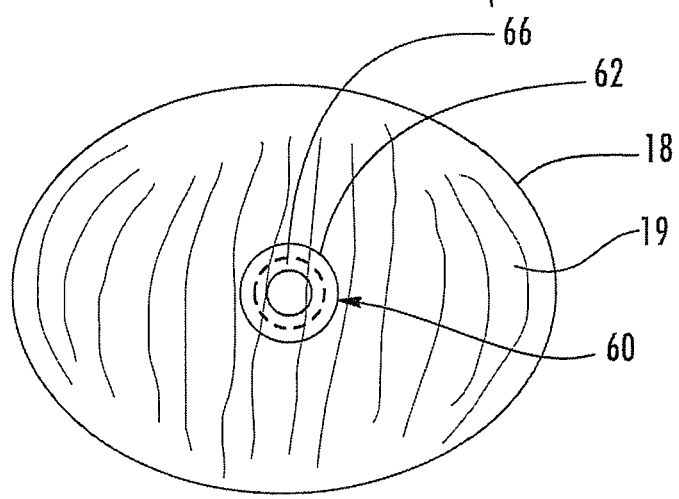
FIG. 2 is a perspective view of a retainer.
Figure 3:
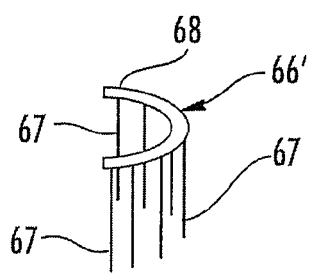
FIG. 3 is an enlarged view taken from the direction in FIG. 1.

Referring now specifically to the drawings, and the illustrative embodiments depicted therein, a medical device 12 includes a wall 18 configured to the size and shape of a portion of a cavity or hollow organ lined with the mucosa and a fixation mechanism 60 that is adapted to fix wall 18 with the portion of the cavity or hollow organ (FIGS. 1 through 3). The fixation mechanism may include one or more openings 62 in wall 18 that are large enough to receive a section of the mucosa extending into the opening upon insertion of the medical device within the cavity or hollow organ. Because of an interference fit between wall 18 and the portion of the cavity or hollow organ, the mucosa tends to bulge into opening(s) 62. While fixation mechanism 60 may employ techniques, such as suction, clasping, or the like, to draw the mucosa into opening(s) 62, opening(s) 62 may be sized to cause the mucosa to bulge sufficiently into the openings as a result of the placement of device 12 to provide fixation. Once the mucosa has entered the openings, the medical device should remain anchored until it is intentionally removed. Fixation mechanism 60 may be used to resist shear force, such as that created by peristalsis and thereby functions as an anti-migration mechanism. In the illustrated embodiments, the portion of wall 18 that does not include opening(s) 62 is a generally impervious surface having a surface area that is larger than an area of opening(s) 62. This reduces tendency for erosions of the mucosa and formation of ulcers. Also, in the illustrated embodiments, capture of the mucosa is limited to the areas at opening(s) 62 thus making removal of the medical device easier. In the illustrative embodiment, opening(s) 62 has a diameter or width that is at least on an order of magnitude of 1.0 mm or greater to receive a sufficiently large bulge of mucosa to provide fixation. It should be understood that the term mucosa is intended to include submucosa. Also, it should be understood that the tissue bulging into opening(s) 62 may include muscularis and serosa as well as mucosa.

In the illustrative embodiments, medical device 12 is shown as an esophageal stent. However, the illustrated techniques may be applied to a bariatric device of the type disclosed in International Publication Nos. WO 2006/044640 A1 and WO 2008/101048 A2, by Baker et al. for a BARIATRIC DEVICE AND METHOD, the disclosures of which are hereby incorporated herein by reference in their entirety. Such bariatric device includes a body having a radially expandable wall thereby defining a transverse passage, or lumen through the body. The body is designed to conform to the shape and size of the abdominal portion of the esophagus, the esophageal-gastric junction and/or the proximal cardiac portion, or cardia, of the patient's stomach. The wall may be a self-extendable, or self-expanding, wall. Alternatively, it may be created by an extendable wall, such as a balloon-extendable wall. The medical device may also be an anti-reflux device, a nasal gastric tube, an intestinal sleeve, other gastrointestinal device or other such medical device as is known in the art.

A retainer 66 may be provided to retain the section of the mucosa within opening(s) 62. Retainer 66 retains the section of the mucosa within opening(s) 62 while maintaining perfusion of the mucosa. Retainer 66 may have a penetrating component which penetrates the mucosa to help retain the section of the mucosa within opening(s) 62. Retainer 66 may have a pressure component which puts pressure on the section of the mucosa to help retain the section of the mucosa within opening(s) 62. The pressure component applies sufficient pressure to retain the section of the mucosa, but not enough pressure to cause ischemia which can lead to necrosis. It should be understood that retainer 66 may include a penetrating component, a pressure component, or both.

Wall 18 has an outer surface 20 and an inner surface 19. Inner surface 19 may define a lumen 63. Retainer 66 may be accessible from within lumen 63 to detach wall 18 from the mucosa in a manner that will be described in more detail below. This facilitates placement and removal of the medical device through a natural orifice, such as endoscopically, or the like. Opening 62 may be a plurality of openings, each of which is large enough to receive a section of the mucosa extending into the opening.

Retainer 66 may be used with fixation mechanism 60 (FIG. 2). Retainer 66 includes a penetration component having a base 68 and a plurality of elongated members, such as needles or tines 67 that interconnects the sections of the mucosa at said plurality of openings. Retainer 66 may be formed to the size and shape of lumen 63 with needles 67 arranged to correspond to positions of openings 62. This allows the physician to first position medical device 12 in the hollow organ or cavity, with wall 18 configured to press against the surface of the organ or cavity thereby causing the mucosa to bulge through openings 62. Retainer 66 can then be moved axially along lumen 63 with needles 67 penetrating the mucosa extending through each opening. This will not significantly interfere with perfusion of the mucosa. When it is desired to remove the medical device, retainer 66 is removed from within lumen 63. Any remaining mucosa can be removed, if desired, by ablation and the medical device moved or removed.

Fixation mechanism 60 may further include retainer 66' in the form of material surrounding opening 62 that causes a fibrotic tissue response in the mucosa extending through the opening (FIG. 3). While retainer 66' may take awhile to assist in retaining the section of the mucosa in opening 62 until the fibrotic tissue response occurs, it may assist retainer 66 in long-term fixation of medical device 12 and may allow retainer 66 to be bioabsorbable. To assist release of the mucosa retained in openings 62 by the fibrotic tissue response-inducing material, known ablation techniques may be applied within lumen 63 to diminish the mucosa bulging in openings 32. Such ablation techniques are relatively non-harmful to the patient. An optional prying tool 65 may be used to pull wall 18 away from the mucosa in openings 62, such that the tissue releases from the openings.

Alternatively, the retainer having a penetrating component could be an elongated member (not shown), such as a suture, that is passed by the physician through the mucosa extending into the lumen to capture the mucosa at openings 62. Alternatively, a plurality of retainers may be used, one for each of the openings.

Figure 4:
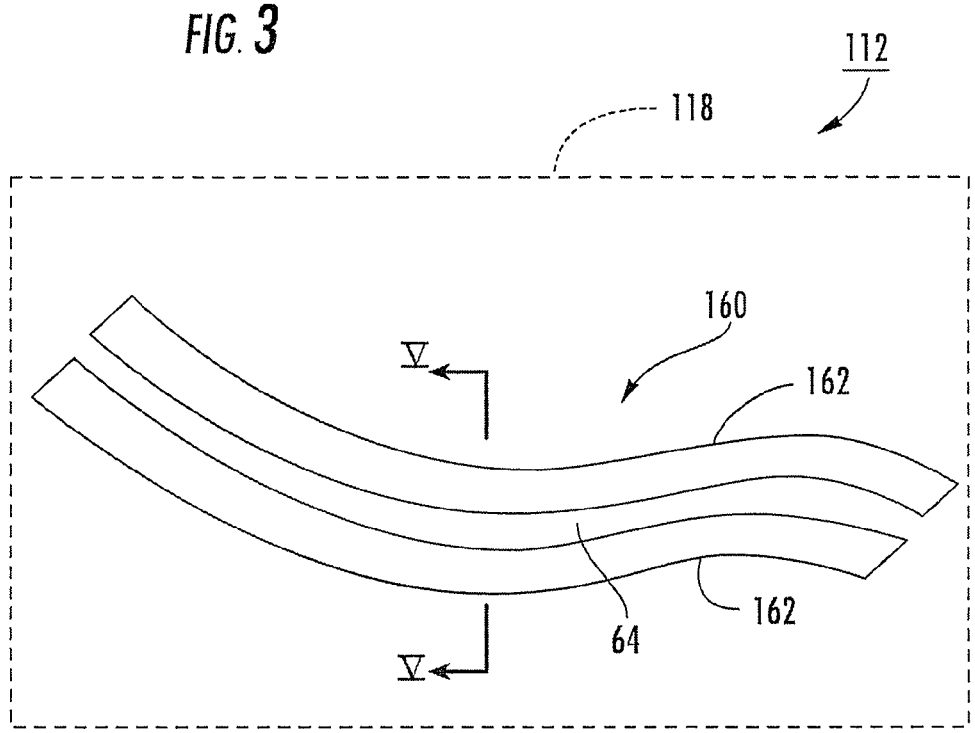
FIG. 4 is a side elevation of another embodiment of mucosal capture fixation of a medical device.
Figure 5:
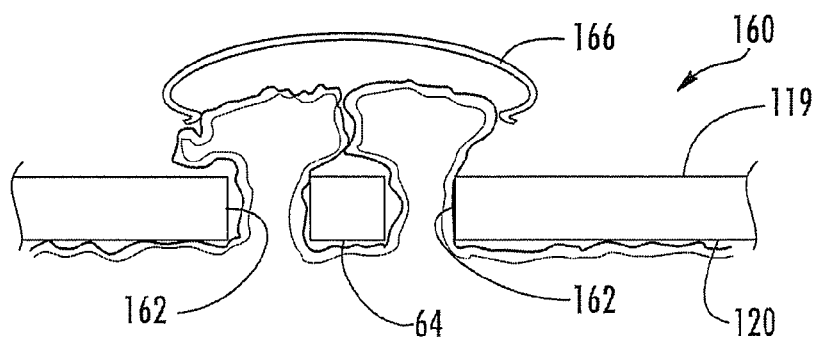
FIG. 5 is an enlarged sectional view taken along the lines IV-IV in FIG. 4.

An alternative embodiment of a medical device 112 has a wall 118 that defines an outer surface 120 and an inner surface 119 (FIGS. 4 and 5). Inner surface 119 may define a lumen (not shown). Wall 118 is configured to the size and shape of a hollow organ or cavity that is lined with the mucosa. Medical device 112 includes a fixation mechanism 160 that is adapted to fix wall 118 with the mucosal tissue lining the hollow organ or cavity. Fixation mechanism 160 may be adapted to be disabled from within the lumen defined by wall 118 in order to detach the medical device from the tissue.

Fixation mechanism 160 is in the form of one or more openings, such as through-openings 162 in wall 118, and at least one retainer that captures the mucosa extending through said opening into the lumen. In the illustrated embodiment fixation mechanism 160 includes at least two openings 162 that are closely spaced, thereby defining tissue apposition openings. The tissue apposition openings are separated by a spacer or bridge 64. As the mucosa passes through openings 162, the bulges of the mucosa tend to bridge spacer 64 and come together in apposition.

Openings 162 are of a size to encourage the tissue, such as the mucosa, to pass through the openings upon insertion of the medical device 112 upon deployment of the device. A retainer 166 may be utilized to retain the mucosa captured in openings 162. The retainer, such as a clip, may be used to retain the sections of the mucosa within openings 162. Clip 166 may join the bulges of the mucosa in apposition. Clip 166 may have a pressure component by applying pressure to the sections of the mucosa within opening(s) 162. The engaging ends of clip 166 may also be configured with a penetrating component to penetrate the sections of the mucosa. Retainer 166 may also be in the form of techniques used to promote fusion of the sections of the mucosa in apposition, such as by abrading the tissue, utilizing a sclerosant agent, or the like. This assists in retaining the sections of the mucosa in openings 162.

Although two openings and one spacer are illustrated, the skilled artisan would recognize that a greater or lesser number of openings and spacers may be utilized. The layout of the openings may be arranged to accommodate the structure of the wall of the medical device. For example, if wall 118 included a spiral structural member, such as a wire mesh, the tissue apposition openings could be spirally formed, as illustrated in FIG. 4, between the wraps of the structural member. The clip can be made of a bioabsorbable material with the fusion of the sections of the mucosa in apposition used for long-term fixation once the clip resolves. To remove medical device 112, the retainer can be accessed and removed from within the lumen, such as endoscopically, and any fused mucosa removed, such as by ablation. Medical device 112 can then be moved within the organ or cavity or removed from the patient.

Clip 166 may, alternatively, have a portion made of a fastener, such as Velcro®, and attach over the sections of the mucosa extending through openings 162 by attaching to surface 119 adjacent to the openings. Other variations will be apparent to the skilled artisan.

In yet a further embodiment, a medical device 212 includes a wall 218 that is generally configured to the size and shape of a hollow organ or cavity of the body. Medical device 212 includes a fixation mechanism 260 including an opening 262 defined between two moveable portions of wall 218. Opening 262 spans the length of wall 218 in the direction of the central axis of the generally tubular shape of the wall. Fixation mechanism 260 may further include a retainer 266 defined by opening 212. Retainer 266 has a pressure component, wherein opening 262 is capable of both receiving a section of the mucosa and putting sufficient pressure on the section of the mucosa to retain the mucosa in the opening. However, the pressure is not high enough to cause ischemia of the mucosa.

Figures 6, 7:
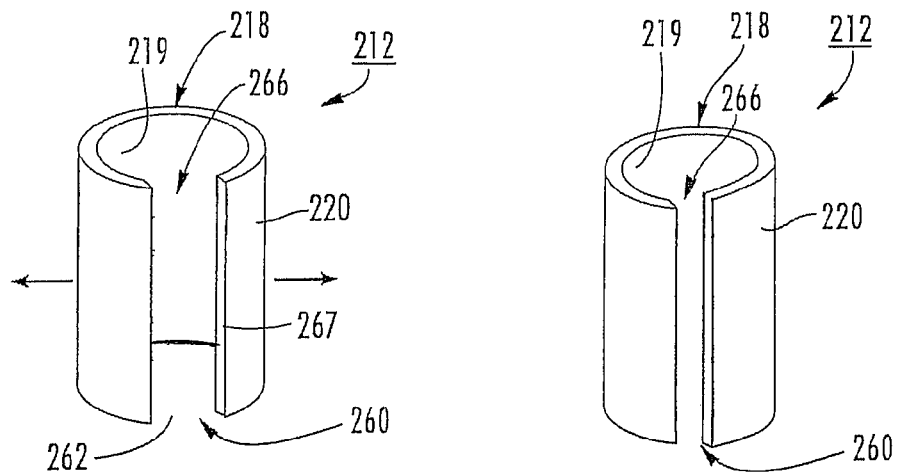
FIG. 6 is a perspective view of another embodiment of mucosal capture fixation of a medical device in an expanded posture.
FIG. 7 is the same view as FIG. 6 showing the medical device in a relaxed posture.

Operation of medical device 212 can be described with respect to an esophageal stent for illustration purposes. Medical device 212 is selected to provide an interference fit with the esophagus. It may be delivered in the state illustrated in FIG. 7 using conventional techniques, such as an over tube. Once it is in the desired position, wall 218 is expanded such as by using a balloon or other tool, which may cause dilation of the esophagus. This causes wall 218 to assume the state illustrated in FIG. 6, thereby allowing the mucosa to bulge into opening 262. The wall is then allowed to relax to the state illustrated in FIG. 7 by releasing of the balloon or other tool. The mucosa will be retained in opening 262 with retainer 266.

Figures 8, 9:
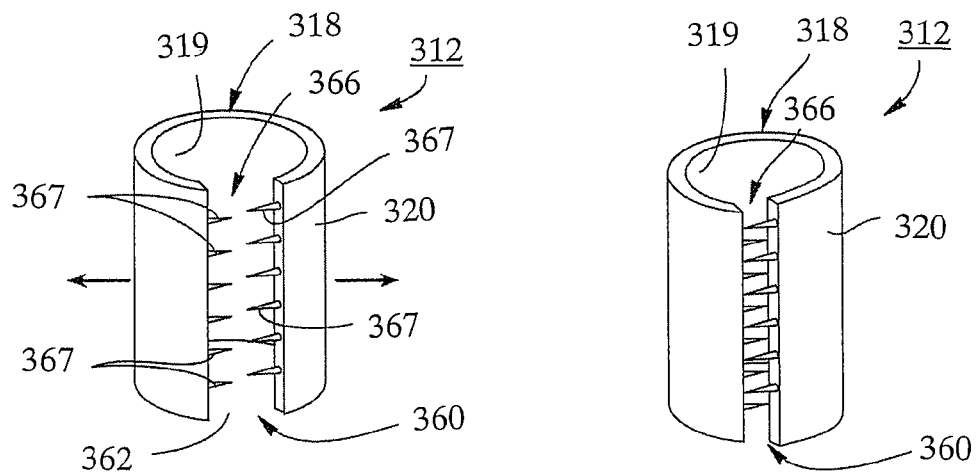
FIG. 8 is the same view as FIG. 6 of an alternative embodiment thereof.
FIG. 9 is the same view as FIG. 7 of the embodiment in FIG. 8.

In another embodiment illustrated in FIGS. 8 and 9, a medical device 312 includes retainer 366 that is made up of the same pressure component of retainer 266 but further includes a penetrating component in the form of a series of needles or tines 367 that extend from one or both edges of the opening toward the opposite edge. A section of the mucosa is received in opening 362 by separating the moveable portions of wall 318, as illustrated by the arrows in FIG. 8. With the mucosa bulging into opening 362, the force is removed from wall 218 allowing it to return to the configuration shown in FIG. 9. The mucosa is retained by the needles of the retainer being moved together by the moveable portions of the wall as well as the force component previously described.

Figure 10:
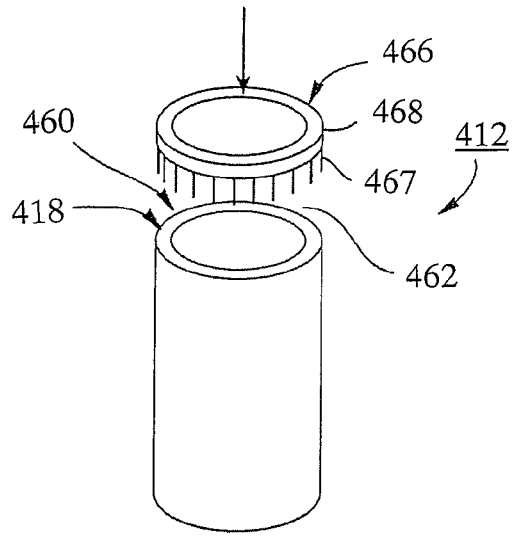
FIG. 10 is a perspective view of another embodiment of mucosal capture fixation of a medical device.

In yet a further embodiment, a medical device 412 including a wall 418, which is configured to the size and shape of the hollow organ or cavity in which it is placed, has a fixation mechanism 460 (FIG. 10). Fixation mechanism 460 includes an opening 462 at an end of wall 418. With wall 418 forming an interference fit with the mucosa of the hollow organ or cavity, the mucosa will bulge over the end of wall 418 to provide retention. Fixation mechanism 460 may further include a retainer 466 having a series of needles or tines 467 that are arranged in order to engage the bulge of the mucosa when retainer 466 is moved axially into juxtaposition with wall 418. Retainer 466 could be initially moveably connected with wall 418 or could be a separate piece, as illustrated in FIG. 10. Also, another such retainer could be applied to an opposite end of wall 418.

Other embodiments will be apparent to the skilled artisan. For example, the wall defining the medical device may be made up of concentric cylinders that can be radially rotated with respect to each other. A fixation mechanism may be provided in the form of each of the cylinders defining an opening in its wall that can be moved into registry with the opening in the other cylinder by rotation of the cylinders to capture a bulge of the mucosa and apply pressure to the mucosa. A penetrating component can be applied to the retainer by the placement of needles or tines at the openings. The mucosa can be captured in the opening formed by rotating the cylinders in one radial direction to align the openings in the cylinders. The captured mucosa can be retained by rotation of the cylinders in the opposite radial direction to reduce the size of the opening, apply pressure to the mucosa and force the needles or tines toward each other. The rotation can be accomplished by a tool, such as a balloon, that is inserted in the device after placement to engage the innermost cylinder to rotate that cylinder. The tool is removed after the fixation mechanism is engaged.

It should be understood that retainers 60, 60', 160, 260, 360 and 460 may be made from a bioabsorbable material, a non-absorbable material, or a combination of both.

Changes and modifications in the specifically described embodiments can be carried out without departing from the principles of the invention which is intended to be limited only by the scope of the appended claims, as interpreted according to the principles of patent law including the doctrine of equivalents.

The embodiments of the invention in which an exclusive property or privilege is claimed are defined as follows:

1. A method of implanting a medical device in a hollow organ or cavity lined with mucosa, said method comprising:
    positioning a medical device having an expandable wall in the hollow organ or cavity lined with mucosa, said wall defining a lumen with proximal and distal ends thereof and configured to the size and shape of a portion of the organ or cavity;
    causing said wall to expand when positioned in the portion of the hollow organ or cavity in order to press said wall against the mucosa of the hollow organ or cavity;
    said wall having at least two adjacent openings separated by a bridge, said at least two adjacent openings being between said proximal and distal ends, each of said openings having a size that is large enough to cause the mucosa to bulge into that opening in a manner that maintains perfusion of the mucosa when said wall is expanded in the portion of the hollow organ or cavity; and
    said adjacent openings being close enough together that the mucosa that bulges into said openings comes together over said bridge to fix said medical device in said hollow organ or cavity.

2. The method as claimed in claim 1 including applying suction to the mucosa that bulges into said openings.

3. The method as claimed in claim 1 including applying at least one retainer across the mucosa that bulges into said openings, said at least one retainer comprising at least one chosen from (i) a pressure component that is adapted to apply pressure sufficient to retain mucosa that bulges into said openings and (ii) a penetrating component that is adapted to penetrate mucosa that bulges into said openings.

4. The method as claimed in claim 1 wherein said wall is made at least in part of a bioabsorbable material.

5. The method as claimed in claim 1 wherein said openings have a size that has an order of magnitude of at least 1.0 millimeter.

6. The method as claimed in claim 1 wherein said wall comprises a generally impervious surface having a surface area that is larger than an area of said at least two adjacent openings.

7. The method as claimed in claim 1 including subsequently removing said medical device including removing the bulged mucosa from said openings.

8. The method as claimed in claim 1 wherein said medical device comprises at least one chosen from an esophageal stent, an anti-reflux device, a nasal gastric tube, an intestinal sleeve, and a bariatric device.

9. A method of implanting a medical device in a hollow organ or cavity lined with mucosa, said method comprising:
    positioning a medical device having an expandable wall in the hollow organ or cavity lined with mucosa, said wall defining a lumen with proximal and distal ends thereof and configured to the size and shape of a portion of the organ or cavity;
    causing said wall to expand when positioned in the portion of the hollow organ or cavity in order to press against the mucosa of the hollow organ or cavity;
    said wall having at least two adjacent openings separated by a bridge, said at least two adjacent openings being between said proximal and distal ends, each of said openings having a size that is large enough to cause the mucosa to bulge into that opening in a manner that maintains perfusion of the mucosa when said wall is expanded in the portion of the hollow organ or cavity, said adjacent openings being close enough together that the mucosa that bulges into said openings comes together over said bridge to fix said medical device in said hollow organ or cavity; and
    promoting fusion of the mucosa that bulges into said openings.

10. The method as claimed in claim 9 wherein said promoting fusion of the mucosa comprises abrading the mucosa that bulges into said openings.

11. The method as claimed in claim 9 wherein said promoting fusion of the mucosa comprises applying a fusion agent to the mucosa that bulges into said openings.

12. The method as claimed in claim 11 wherein said fusion agent comprises a sclerosant.

13. The method as claimed in claim 9 including applying at least one retainer across the mucosa that bulges into said openings, said at least one retainer comprising at least one chosen from (i) a pressure component that is adapted to apply pressure sufficient to retain mucosa that bulges into said openings and (ii) a penetrating component that is adapted to penetrate mucosa that bulges into said openings.

14. The method as claimed in claim 9 including applying suction to the mucosa that bulges into said openings.

15. The method as claimed in claim 14 including subsequently removing said medical device including removing the bulged mucosa from said openings.

16. The method as claimed in claim 14 wherein said medical device comprises at least one chosen from an esophageal stent, an anti-reflux device, a nasal gastric tube, an intestinal sleeve and a bariatric device.

17. The method as claimed in claim 9 wherein said wall is made at least in part of a bioabsorbable material.

18. The method as claimed in claim 9 wherein said openings have a size that has an order of magnitude of at least 1.0 millimeter.

19. The method as claimed in claim 9 wherein said wall comprises a generally impervious surface having a surface area that is larger than an area of said at least two adjacent openings.

* * * * *